(12) United States Patent
Van Bommel et al.

(10) Patent No.: US 12,128,151 B2
(45) Date of Patent: Oct. 29, 2024

(54) DISINFECTION LIGHTING DEVICE, LAMP AND LUMINAIRE USING UV LIGHT

(71) Applicant: SIGNIFY HOLDING B.V., Eindhoven (NL)

(72) Inventors: Ties Van Bommel, Horst (NL); Kars-Michiel Hubert Lenssen, Veldhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/576,827

(22) PCT Filed: Jun. 27, 2022

(86) PCT No.: PCT/EP2022/067546
§ 371 (c)(1),
(2) Date: Jan. 5, 2024

(87) PCT Pub. No.: WO2023/280611
PCT Pub. Date: Jan. 12, 2023

(65) Prior Publication Data
US 2024/0245814 A1    Jul. 25, 2024

(30) Foreign Application Priority Data
Jul. 5, 2021  (EP) .................................... 21183765

(51) Int. Cl.
*A61L 2/10* (2006.01)
*A61L 2/08* (2006.01)
(Continued)

(52) U.S. Cl.
CPC ................ *A61L 2/10* (2013.01); *A61L 2/084* (2013.01); *A61L 2/26* (2013.01); *F21V 33/0064* (2013.01);
(Continued)

(58) Field of Classification Search
CPC ........ A61L 2/084; A61L 2/10; A61L 2/26–28; A61L 2202/11; F21V 33/0064–0068; F21Y 2113/30; F21Y 2115/10
See application file for complete search history.

(56) References Cited

FOREIGN PATENT DOCUMENTS

| EP | 3998116 A1 | 5/2022 |
|---|---|---|
| JP | 2020011856 A | 1/2020 |

(Continued)

*Primary Examiner* — Jason M Han

(57) ABSTRACT

The invention relates to a disinfection lighting device (10) comprising a first light source (14), wherein the first light source (14) comprises a solid-state light source, wherein the solid-state light source comprises one or more light emitting diodes (14a, 14b), lasers and/or superluminescent diodes; wherein the first light source (14) is configured to generate first light source light having a first spectral power distribution, wherein the first spectral power distribution comprises first light source light (140) in the UV wavelength range and/or visible wavelength range, a second light source (13), wherein the second light source (13) is configured to generate second light source light (130) having a second spectral power distribution different from the first spectral power distribution, wherein the second spectral power distribution comprise in the UV wavelength range, wherein the second light source (13) is arranged at a distance D from the first light source (14), the second light source (13) comprises a light input face (13b) configured in a light receiving relationship with the first light source (13), and the second light source (14) comprises a light exit face (13a), wherein the second light source (13) is transmissive for at least, a major, part of the first light source light (140); and wherein the disinfection lighting device (10) is configured to generate lighting device light comprising the second light source light (130) and the first light source light (140) emanating from the light exit face (13a), wherein the disinfection (Continued)

lighting device (10) comprises a light exit window (12), wherein the light exit face (13*a*) is the light exit window (12).

13 Claims, 4 Drawing Sheets

(51) Int. Cl.
*A61L 2/26* (2006.01)
*F21V 33/00* (2006.01)
*F21Y 113/00* (2016.01)
*F21Y 115/10* (2016.01)

(52) U.S. Cl.
CPC ........ *A61L 2202/11* (2013.01); *F21Y 2113/30* (2023.05); *F21Y 2115/10* (2016.08)

(56) References Cited

FOREIGN PATENT DOCUMENTS

| | | |
|---|---|---|
| KR | 20210031229 A | 3/2021 |
| WO | 2017012829 A1 | 1/2017 |
| WO | 2021025063 A1 | 2/2021 |
| WO | 2021025064 A1 | 2/2021 | ns using UV light. The present disclosure further relates to a lamp and a luminaire.

DISINFECTION LIGHTING DEVICE, LAMP AND LUMINAIRE USING UV LIGHT

CROSS-REFERENCE TO PRIOR APPLICATIONS

This application is the U.S. National Phase application under 35 U.S.C. § 371 of International Application No. PCT/EP2022/067546, filed on Jun. 27, 2022, which claims the benefit of European Patent Application No. 21183765.3, filed on Jul. 5, 2021. These applications are hereby incorporated by reference herein.

TECHNICAL FIELD

The present disclosure relates to a disinfection lighting device suitable for disinfecting the air of an area, such as a room in a personal home or office environment using UV light. The present disclosure further relates to a lamp and a luminaire.

BACKGROUND OF THE INVENTION

There is an increasing interest—due to health and safety concerns—to protect people in both personal homes and in office environments from the spread of bacteria and viruses, such as influenza or against the outbreak of novel viruses like the recent COVID-19 pandemic. In the consumer domain (single) air purifying devices are used of which some have ionizing generators included that can kill bacteria and viruses when air ion density is at the correct level, thus improving the indoor air quality (IAQ). Alternatively, ultraviolet (UV) light emitted from ultraviolet light sources can also be used for disinfection.

There is a need to improve the performance and/or safety of disinfection lighting based on UV light emission and accordingly this disclosure proposes a disinfection device combining UV light emission with a specific constructional configuration, allowing an effective disinfection of large areas, such as personal homes and in office environments.

WO2021025063 and WO2021025064 both disclose a disinfection lighting device with an auxiliary UV source for ignition of a first UV source.

SUMMARY OF THE INVENTION

According to a first aspect of the disclosure a disinfection lighting device is proposed, comprising a first light source, wherein the first light source comprises a solid-state light source, wherein the solid-state light source comprises one or more light emitting diodes, lasers and/or superluminescent diodes; wherein the first light source is configured to generate first light source light having a first spectral power distribution, wherein the first spectral power distribution comprises first light source light in the UV wavelength range and/or visible wavelength range, a second light source, wherein the second light source is configured to generate second light source light having a second spectral power distribution different from the first spectral power distribution, wherein the second spectral power distribution comprises second light source light in the UV wavelength range, for example essentially only in the UV wavelength range, such as for at least 90% of its photoemission in the UV wavelength range, wherein the second light source is arranged at a distance D from the first light source, the second light source comprises a light input face configured in a light receiving relationship with the first light source, and the second light source comprises a light exit face, wherein the second light source is transmissive for at least (a major) part of the first light source light; and wherein the disinfection lighting device is configured to generate lighting device light emanating from the light exit face and comprising the second light source light and the first light source light.

This design provides a compact and effective disinfecting apparatus wherein UV light with different spectral power distributions is mixed and emitted towards the environment for disinfecting purposes. For an improved disinfection performance, both the first light source and second light source not only are simultaneously in operation (meaning "on-status") during an ignition period, which is typically in the order of about a minute, but preferably are simultaneously in the "on-status" after the ignition for at least a major fraction, for example at least during 50%, such as 80% even up to and including 100%, of their individual normal on-status period, typically during more minutes, or hours or even days. In the normal on-status the respective light source is in stable operation and emits its respective light source light.

In particular, the first spectral power distribution comprises first light source light in the UV wavelength range, wherein the first spectral power distribution has a first dominant wavelength, $\lambda 1$, and the second spectral power distribution has a second dominant wavelength, $\lambda 2$, wherein, $\lambda 2 < \lambda 1$. Preferably, the second dominant wavelength, $\lambda 2 < 235$ nm. More preferably, the second dominant wavelength, $\lambda 2$, is in a range from 190 to 230 nm. This wavelength range is relatively safe and/or provides a high disinfection performance. Furthermore, in a preferred example, the first dominant wavelength, $\lambda 1$, ranges 315 nm $> \lambda 1 > 235$ nm. More preferably, the first dominant wavelength, $\lambda 1$, ranges 315 nm $> \lambda 1 > 280$ nm (i.e. UV-B light), or the first dominant wavelength, $\lambda 1$, ranges 280 nm $> \lambda 1 > 235$ nm (i.e. near UV-C light). UV-B light is most effective to be used for vitamin D lighting (i.e. an optimum between maximum vitamin D production in the skin and providing less impact on the skin). Dominant wavelength in this context means the highest peak in emission at said wavelength in number of photons.

According to a further example according to the disclosure, the first light source light has a first spectral power distribution; and the first light source light is white light having a correlated color temperature or color temperature (CT) in a range from 2000 to 8000 K and a color rendering index (CRI) of at least 70. The CRI is preferably >75, more preferably CRI>80, most preferably CRI>85, such as for example CRI=90.

In a further effective example, the second light source is not a solid state light source such as for example a gas discharge light source. In certain embodiments, the second light source has a disk or plate shape. This allows the disinfection lighting device to be designed with limited constructional dimensions, in particular as to its height or depth dimension, capable to be implemented in all kinds of applications in a personal home or office space environment. In particular, with this embodiment an advantageous constructional geometry of a large UV light exiting surface area is obtained, which configuration thus exhibits an effective disinfecting functionality.

Additionally, the first light source, and optionally the second light source, is arranged in a housing comprising one or more light reflective inner walls. Herewith an improved exiting of UV light is achieved, wherein the concentration of UV light results in a more effective disinfecting functionality. the concentration of emitted UV light is further improved in an example, wherein the housing is formed as a tapered reflector; wherein the tapered reflector has a narrow end face, a wide end face, as well as an edge wall, preferably an (closed) annular edge wall, connecting the narrow end face and the wide end face, wherein the first light source is closer arranged to the narrow end face compared to the wide end face, and the second light source is closer arranged to the wide end face compared to the narrow end face.

In particular, the second light source is arranged at the wide end face.

In a further example having an improved light distribution, the lighting device light comprises collimated first light source light and uncollimated second light source light. More specifically, an example of the disinfection lighting device with improved light distribution has more than 90% of the first light source light in the lighting device light emanating directly from the light exit face. Directly in this context means that light is emanating from the light exit face without being reflected at the light reflective surface of the inner wall of the housing.

In an example, the disinfection lighting device comprises a light exit window, wherein the light exit face is the light exit window. Also this example allow the disinfection lighting device to be designed with limited constructional dimensions, capable to be implemented in all kinds of lighting applications in a personal home or office space environment.

For a proper operation, the disinfection lighting device may comprise a controller for individually controlling the first light source and the second light source, wherein the disinfection lighting device is configured to generate lighting device light having a controllable spectral power distribution. Herewith, the operational conditions of the disinfection lighting device and hence the disinfecting functionality of the device can be readily set.

Furthermore, the disclosure also pertains to a lamp comprising the disinfection lighting device according to the disclosure outlined in this application, wherein the lamp further comprises a cap for electrically and mechanically connecting the lamp to a socket, for example a socket of a luminaire. Accordingly, this allows the disinfection lighting device according to the disclosure to be retrofitted in an existing luminaire.

Hence, the invention also relates to a luminaire comprising a housing and accommodating at least one disinfection device and/or lamp according to the invention in said housing. The luminaire further comprises mains contact means for connecting to a power source and electrical contact means, for example a socket, for connecting to a disinfection device. The luminaire and/or the lamp and/or the disinfection device may comprise a filter, for example arranged at the light exit face and/or at the light exit window. Said filter blocks undesired radiation generated by the first and/or second light source from being emanated by the disinfection device, the lamp and/or the luminaire. For example, if the second light source is an excimer lamp, such as an KrCl excimer lamp, which typically generates far UVC at a dominant wavelength of about 222 nm, some undesired, potentially harmful, emission in the deep UVC wavelength range of 250-260 nm is also generated, and said undesired emission is then blocked, either by reflection and/or absorption, by the filter. Thus, a disinfection device, lamp and/or luminaire is provided which is safer to humans.

BRIEF DESCRIPTION OF THE DRAWINGS

The invention will now be discussed with reference to the drawings, which show in.

DETAILED DESCRIPTION OF THE INVENTION

Figure 1:
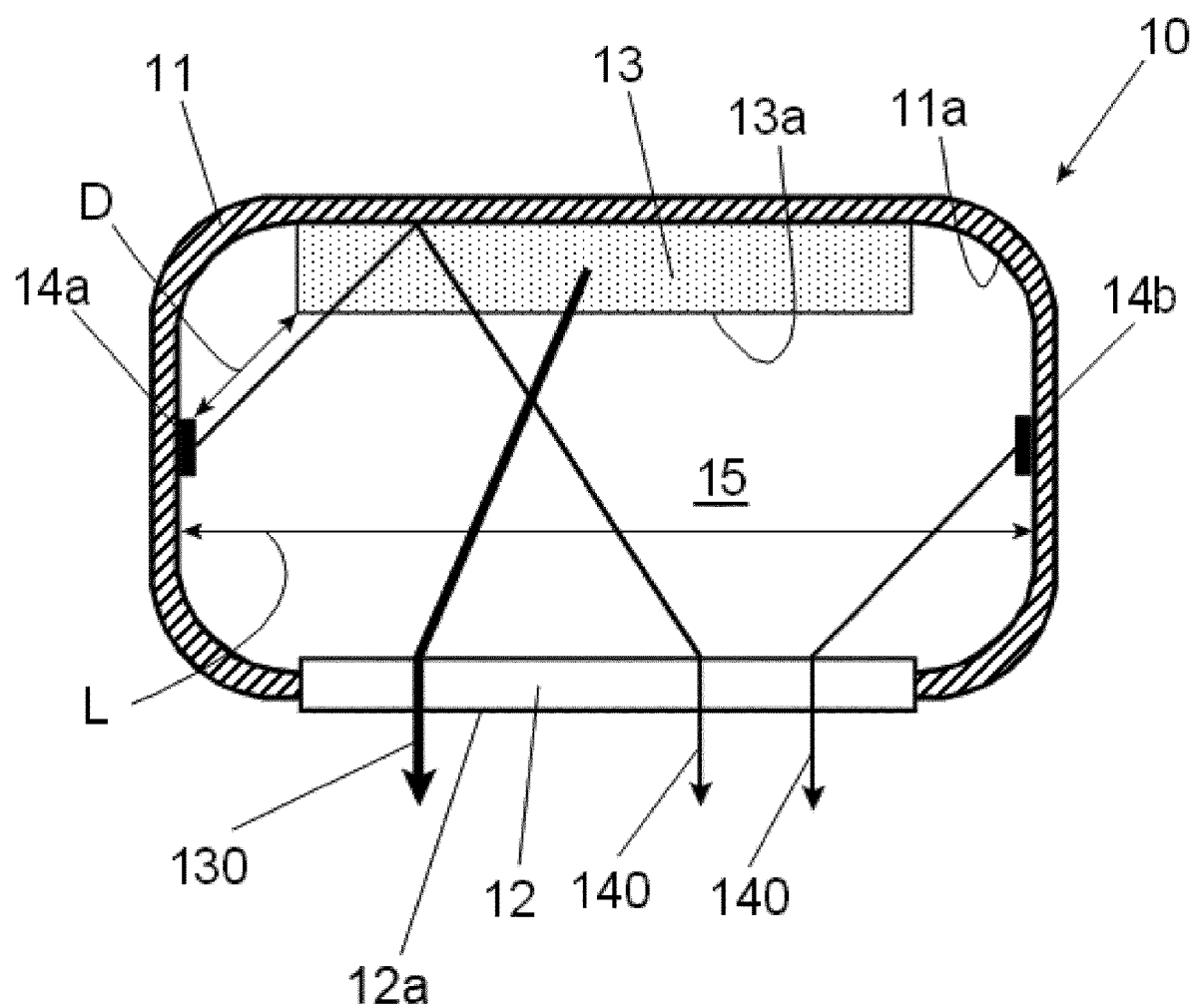
FIGS. 1-3 several examples of an ultraviolet light emitting apparatus according to the disclosure.

For a proper understanding of the invention, in the detailed description below corresponding elements or parts of the invention will be denoted with identical reference numerals in the drawings.

FIG. 1 shows a first example of a disinfection lighting device according to the disclosure, denoted with reference numeral 10. In a preferred embodiment the disinfection lighting device 10 comprises a first light source 14 (14a-14b) and a second light source 13.

Specifically, the first light source 14 (14a-14b) is composed of a solid-state light source consisting of one or more light emitting diodes, lasers and/or superluminescent diodes (14a-14b). When powered, the first light source 14 generates first light source light having a first spectral power distribution. In the Figures the first light source light is denoted with reference numeral 140. For the sake of clarity, the first light source light 140 is depicted as single lines illustrating a light beam, however it should be understood that the first light source 14 emits broad, spatial distributed first light source light 140.

It should be noted, that the first spectral power distribution as emitted by the first light source 14 (14a-14b) comprises the first light source light 140 in the UV wavelength range and/or visible wavelength range.

Additionally, the disinfection lighting device 10 comprises a second light source 13. The second light source 13 generates and emits second light source light, which is denoted with 130. For the sake of clarity, although the second light source light 130 is depicted as single lines illustrating a light beam, also here it should be understood that the second light source 13 emits broad, spatial distributed second light source light 130 having a second spectral power distribution.

The second spectral power distribution of the second light source light 130 is different from the first spectral power distribution of the first light source light 140.

Similarly, the second spectral power distribution as emitted by the second light source 13 comprises the second light source light 130 in the UV wavelength range.

Preferably, the disinfection lighting device 10 comprises a housing 11 in which the first and second light sources 14 and 13 are accommodated within the inner chamber 15 of the housing 11.

As shown in the Figures, the second light source 13 is arranged or disposed at a distance D from the first light source 14 (14a-14b), with the distance D being defined as the shortest distance between both light sources 13-14. In particular, the second light source 13 comprises a light input face 13a that is configured in a light receiving relationship with the first light source 14 (14a-14b). Similarly, the second light source 13 comprises a light exit face 13a, making the second light source 13 transmissive for at least (a major) part of the first light source light 140.

Figure 2:
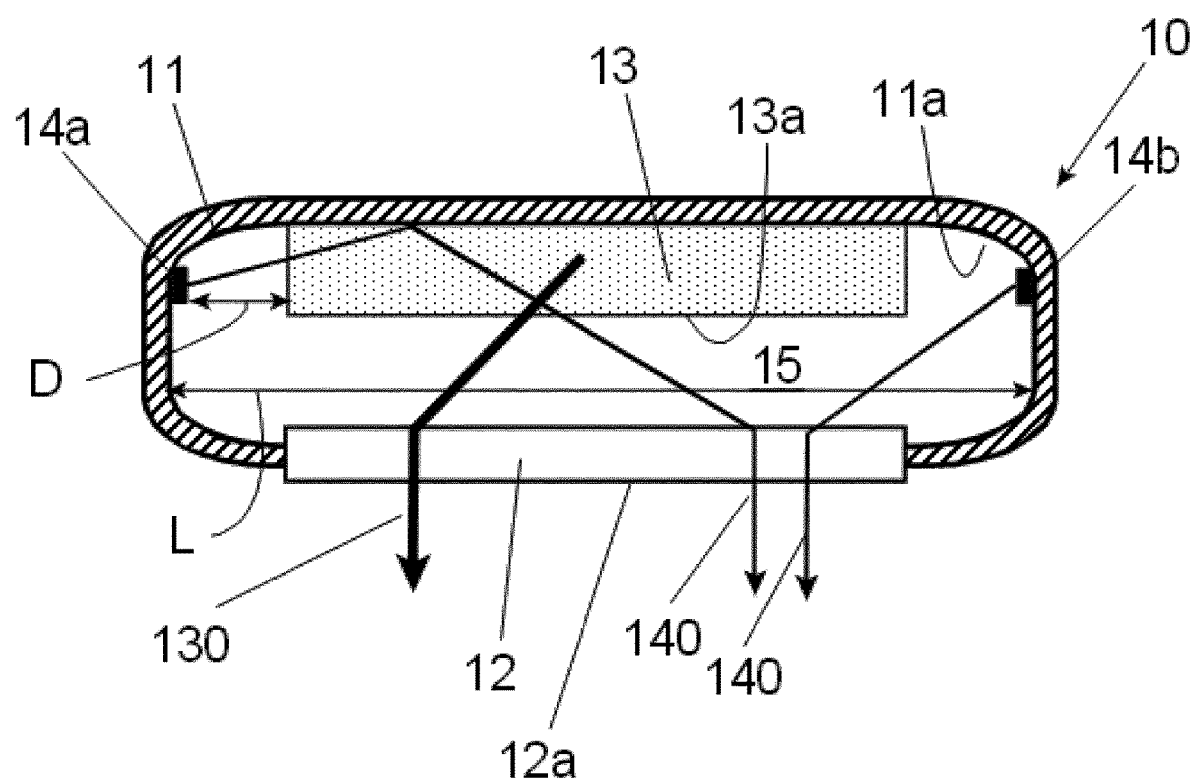

In FIG. 1, the second light source 13 is arranged or disposed at a larger distance D from the first light source 14 (14a-14b) compared to the smaller distance D as in the embodiment of FIG. 2, this due to the smaller height/depth dimension of the FIG. 2 embodiment.

In particular, the (shortest) distance D between the second light source 13 and the first light source 14 is preferably 0.9 L>D>0.1 L, more preferably 0.8 L>D>0.2 L, and most preferably 0.7 L>D>0.3 L, where L is the length dimension of the disinfection lighting device 10, e.g. measured along the longitudinal axis of the disinfection lighting device 10. See the Figures.

In term of absolute values, it is preferred that 20 cm>D>1 cm, more preferably 15 cm>D>2 cm, and most preferably 10 cm>D>3 cm.

Accordingly, the disinfection lighting device 10 is structured to generate a mix of lighting device light comprising the second light source light 130 and the first light source light 140. As the second light source 13 is transmissive for at least (a major) part of the first light source light 140, a mix of lighting device light composed of second light source light 130 and first light source light 140 emanates from the light exit face 13a of the second light source 13 and is allowed to exit the disinfection lighting device 10 via a light exit window 12 provided in the housing 11 (FIG. 1 and FIG. 2).

In the examples of FIG. 1 and FIG. 2 the first light source light 140 generated and emitted by the first light source 14 (14a-14b) can exit the light exit window 12 either directly or via the light transmissive second light source 13. In either situation both second light source light 130 and first light source light 140 exit the disinfection lighting device 10 as a mix of lighting device light.

This design provides a compact and effective disinfection lighting device wherein UV light with different spectral power distributions (composed of second light source light 130 and first light source light 140) is mixed and emitted towards the environment for disinfecting purposes.

For creating improved light distributions, the lighting device light comprises collimated first light source light 140 and uncollimated second light source light 130. More specifically, the design of the disinfection lighting device 10 is such, that the mix of the lighting device light emanating from the light exit face 12a is composed of more than 90% of the first light source light 140.

In embodiments, the first light source light 140 has a first spatial light distribution having a full width at half maximum (FWHM)<25°, preferably a FWHM<20°, more preferably a FWHM<15°, most preferably a FWHM<15°.

In embodiments, the second light source light 130 has a second spatial light distribution having a FWHM>30°, preferably a FWHM>35°, more preferably a FWHM>40°, most preferably a FWHM>45°.

A preferred specification of both first and second light sources 14-13 pertain to a first spectral power distribution comprising first light source light 140 with the first spectral power distribution having a first dominant wavelength $\lambda 1$, and a second spectral power distribution comprising second light source light 13 having a second dominant wavelength $\lambda 2$.

Preferably, $\lambda 2 < \lambda 1$. In a preferred example, the second dominant wavelength $\lambda 2 < 235$ nm. Furthermore, in another preferred example, the first dominant wavelength $\lambda 1$ ranges 315 nm>$\lambda 1$>235 nm.

In further detailed specifications of a disinfection lighting device according to an example, the first spectral power distribution comprises first light source light 140 in the visible wavelength range. Preferably, the first light source light 140 is white light having a correlated color temperature or color temperature in a range from 2000 to 8000 K and a color rendering index (CRI) of at least 70.

As to a CRI of at least 70, it is noted that such CRI can be obtained by implementing white LEDs and/or a combination of colored LEDs. For example, a phosphor converted white LED may be used i.e. a blue and/or UV LED with a phosphor for at least partly converting LED light into converted light. The LED light and/or the converted light may be the white light. The CRI is preferably >75, more preferably CRI>80, most preferably CRI>85, such as for example a CRI of 90.

The second light source 13 may be configured as a gas discharge light source and in particular the second light source 13 has a disk or plate shape. The examples of a disk or plate shaped second light source 13 are depicted in the embodiments of FIGS. 1-4. Such disk or plate shaped configurations provide designs of a disinfection lighting device 10 with limited constructional dimensions. Accordingly, such designs allows the disinfection lighting device 10 to be implemented in all kinds of applications in a personal home or office space environment. In particular, with a disk or plate shaped embodiment of the second light source 13 an advantageous constructional geometry of a large UV light exiting surface area can be obtained, which configuration thus exhibits an effective disinfecting functionality.

The second light source 13 may also be a light guide and a UV solid state light emitting UV light. The UV light is coupled into the light guide at a light in-coupling portion/means. The UV light is coupled out by a light outcoupling portion/means e.g. a pattern of reflective dots arranged on a major surface of the light guide preferably the face which is facing the first light source.

The housing 11 may comprise one or more light reflective inner walls 11a, further improving the propagation and transmission of both first light source light 140 and second light source light 130 within the inner chamber 15 and reducing absorption within the disinfection lighting device 10. In addition, an improved exiting of the mix of first light source light 140 and second light source light 130 as lighting device light emanating the light exit face 12a is achieved.

Figure 4:
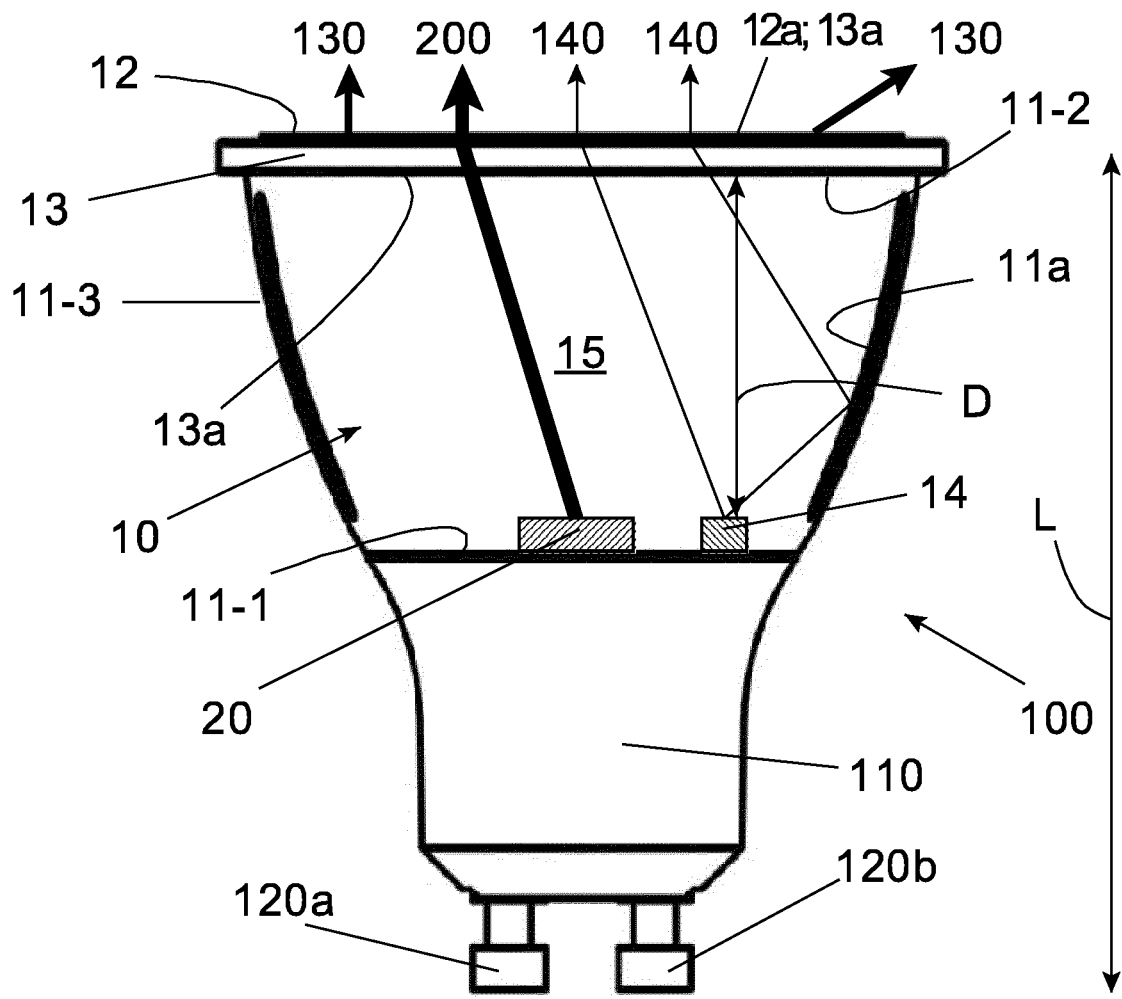
FIG. 4 an ultraviolet light emitting apparatus configured as an illumination device, capable to be retro-fitted in a fluorescent armature.

The concentration of lighting device light emanating the disinfection lighting device 10 is further improved in the example of FIG. 4. In FIG. 4, the housing 11 is formed as a tapered reflector. The tapered reflector has a narrow end face denoted with reference numeral 11-1 and a wide end face 11-2. The narrow end face 11-1 and the wide end face 11-2 are connected by means of edge walls 11-3. In this example, the edge walls 11-3 is formed as one circumferential edge wall 11-3.

The reflector is preferably specular reflective in order to collimate the first light source light 170 beneficially. The reflector has e.g. a conical and/or a parabolic shape.

The narrow end face 11-1 and the wide end face 11-2 have both a longitudinal dimension or a diameter dimension, denoted as $DIM_{narrow}$ versus $DIM_{wide}$. Preferably, the longitudinal/diameter dimension of the wide end face 11-2 is at least twice or more than the longitudinal/diameter dimension of the narrow end face 11-1, in other words $DIM_{wide} > 2 DIM_{narrow}$.

As shown in FIG. 4, the first light source 14 is mounted closer to the narrow end face 11-1 compared to the wide end face 11-2. The second light source 13 is mounted at a position within the housing 11 closer to the wide end face 11-2 compared to the narrow end face 11-1. Preferably, as shown in FIG. 4, the second light source 13 is arranged at the wide end face 11-2.

In all embodiments of FIGS. 1-4, the disinfection lighting device 11 comprises a light exit window 12 for exiting the mix of lighting device light composed of first light source light 140 and second light source light 130.

Figure 3:
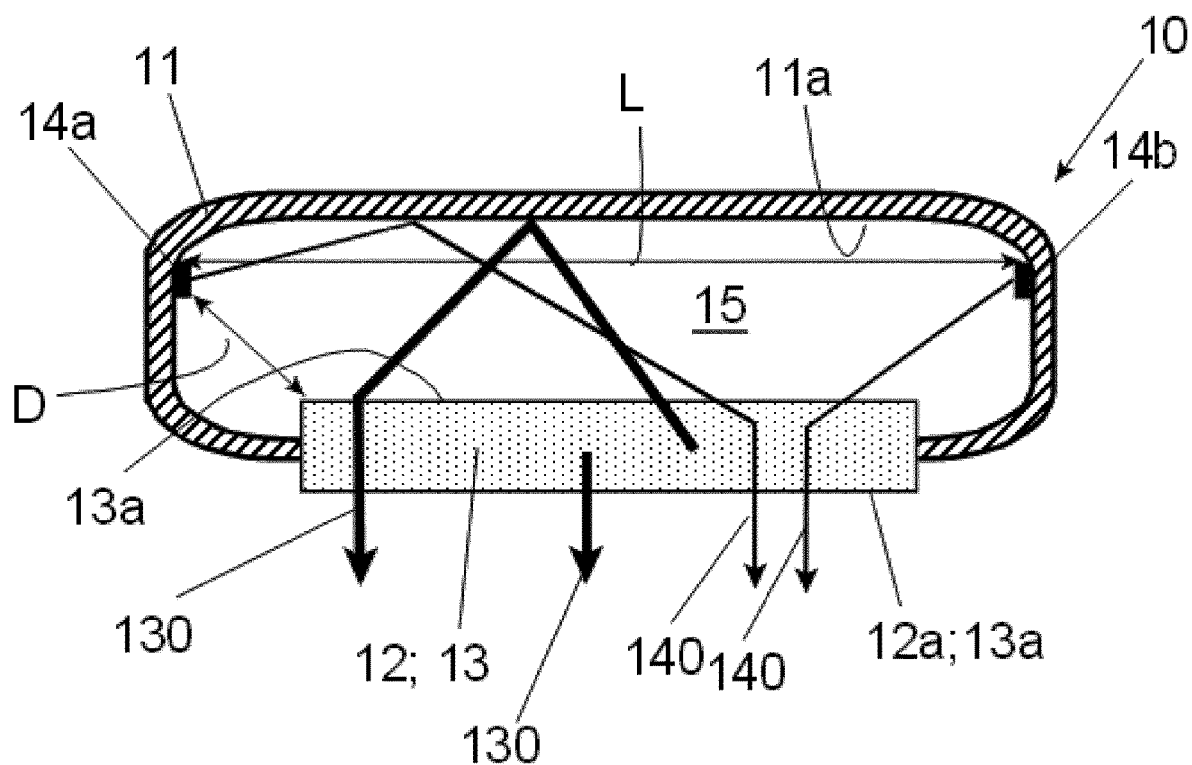

In specific embodiments, as shown in FIGS. 3 and 4, the light exit face 13a of the second light source 13 constitutes the light exit window 12. These examples result in the disinfection lighting devices with limited constructional dimensions, at least in the height/depth dimensions and as such, these designs allow a beneficial implementation in all kinds of lighting applications in a personal home or office space environment.

For a proper operation, the disinfection lighting device may comprise a controller for individually controlling the first light source and the second light source, wherein the disinfection lighting device is configured to generate lighting device light having a controllable spectral power distribution. Herewith, the operational conditions of the disinfection lighting device and hence the disinfecting functionality of the device can be readily set.

The embodiment of FIG. 4 discloses also a lamp 100, which is provided with a disinfection lighting device 10 according to the disclosure. The lamp 100 is provided with a cap 110 with socket pins 120a-120b for electrically and mechanically connecting the lamp 100 to a socket of a luminaire. The lamp 100 is provided with a further regular light emitting source 20 structured for emitting visible light 200. Accordingly, this allows the disinfection lighting device 10 according to the disclosure to be retrofitted in an existing luminaire and designed for combined illumination with visible light 200 as well as environmental disinfection using the mix of the mix of lighting device light composed of first light source light 140 and second light source light 130.

LISTING OF REFERENCE NUMERALS 10 disinfection lighting device (1$^{st}$, 2$^{nd}$, 3$^{rd}$ and 4$^{th}$ example)
11 a housing
11a light reflective surface of inner wall of housing
110 retrofitted housing (4$^{th}$ example)
11-1 narrow end face of housing (4$^{th}$ example)
11-2 wide end face of housing (4$^{th}$ example)
11-3 edge wall of housing (4$^{th}$ example)
12 light exit window
13 second light source
130 second light source light having a second spectral power distribution
14, 14a-14b first light source
140 first light source light having a first spectral power distribution
15 inner chamber of housing
20 further light emitting device for emitting visible light
200 visible light
100 lamp
120a-120b electric connector pins
D distance between the first light source and the second light source
L length dimension of the disinfection lighting device

The invention claimed is:

1. A disinfection lighting device comprising:
a first light source, wherein the first light source comprises a solid-state light source, wherein the solid-state light source comprises one or more light emitting diodes, lasers and/or superluminescent diodes; wherein the first light source is configured to generate first light source light having a first spectral power distribution, wherein the first spectral power distribution comprises first light source light in the UV wavelength range and/or visible wavelength range;
a second light source, wherein the second light source is configured to generate second light source light having a second spectral power distribution different from the first spectral power distribution, wherein the second spectral power distribution comprises second light source light in the UV wavelength range,
wherein the second light source is arranged at a distance D from the first light source, the second light source comprises a light input face configured in a light receiving relationship with the first light source, and the second light source comprises a light exit face,
wherein the second light source is transmissive for at least (a major) part of the first light source light; and
wherein the disinfection lighting device is configured to generate lighting device light emanating from the light exit face and comprising the second light source light and the first light source light,
wherein the disinfection lighting device comprises a light exit window, wherein the light exit face is the light exit window.

2. The disinfection lighting device according to claim 1, wherein the first spectral power distribution comprises first light source light in the UV wavelength range;
wherein the first spectral power distribution has a first dominant wavelength, $\lambda 1$, and the second spectral power distribution has a second dominant wavelength, $\lambda 2$, wherein, $\lambda 2 < \lambda 1$.

3. The disinfection lighting device according to claim 2, wherein $\lambda 2 < 235$ nm.

4. The disinfection lighting device according to claim 3, wherein 315 nm $> \lambda 1 > 235$ nm.

5. The disinfection lighting device according to claim 1, wherein the first spectral power distribution comprises first light source light in the visible wavelength range; and
wherein the first light source light is white light having a correlated color temperature or color temperature in a range from 2000 to 8000 K and a color rendering index of at least 70.

6. The disinfection lighting device according to claim 1, wherein the second light source is a gas discharge light source.

7. The disinfection lighting device according to claim 1, wherein the second light source has a disk or plate shape.

8. The disinfection lighting device according to claim 1, wherein the first light source, and optionally the second light source, is arranged in a housing comprising one or more light reflective inner walls.

9. The disinfection lighting device according to claim 8, wherein the housing is formed as a tapered reflector;
wherein the tapered reflector has a narrow end face, a wide end face, as well as an edge wall connecting the narrow end face and the wide end face,
wherein the first light source is closer arranged to the narrow end face compared to the wide end face, and the second light source is closer arranged to the wide end face compared to the narrow end face, preferably the second light source is arranged at the wide end face.

10. The disinfection lighting device according to claim 9, wherein the lighting device light comprises collimated first light source light and uncollimated second light source light.

11. The disinfection lighting device according to claim 1, wherein the disinfection lighting device is configured to generate lighting device light having a controllable spectral power distribution in that the disinfection lighting device comprises a controller for individually controlling the first light source and the second light source.

12. A lamp comprising the disinfection lighting device according to claim 1, wherein the lamp further comprises a cap for electrically and mechanically connecting the lamp to a socket.

13. A luminaire comprising a housing accommodating a lamp and/or a disinfection device as claimed in claim 1.

* * * * *